United States Patent [19]
Doe

[11] Patent Number: 5,900,535
[45] Date of Patent: May 4, 1999

[54] METHOD AND APPARATUS FOR ULTRASONIC MEASUREMENT OF FUEL QUANTITY AND DENSITY

[75] Inventor: Steve Doe, Camberley, United Kingdom

[73] Assignee: Smiths Industries PLC, London, United Kingdom

[21] Appl. No.: 08/781,820

[22] Filed: Jan. 10, 1997

[30] Foreign Application Priority Data

Jan. 26, 1996 [GB] United Kingdom ............... 9601535

[51] Int. Cl.$^6$ ........................................ G01N 9/00
[52] U.S. Cl. ................................. 73/32 A; 73/597
[58] Field of Search ................. 73/290 V, 304 R, 73/32 R, 24.01, 32 A; 367/908, 99; 340/621; 181/124; 702/54, 55

[56] References Cited

U.S. PATENT DOCUMENTS 4,815,323  3/1989  Ellinger ............................. 73/290 V
5,121,340  6/1992  Campbell ............................ 340/621

FOREIGN PATENT DOCUMENTS 0 384 373  8/1990  European Pat. Off. .
WO 91/19191  12/1991  WIPO .

*Primary Examiner*—Christine K. Oda
*Attorney, Agent, or Firm*—Pollock, Vande Sande & Priddy

[57] ABSTRACT

An ultrasonic fuel-gauging system has a tank with several ultrasonic probes having reflectors spaced along their length. A vibrating cylinder densitometer is located at the bottom of the tank and provides an output to a control unit representative of fuel density at that location. The control unit calculates the speed of sound reflected from the reflector closest to the densitometer and uses this and the density measurement to calculate a fuel constant. The control unit calculates the density of fuel at different heights from the fuel constant and speed of sound measurements from other reflectors. From these density measurements the control unit calculates mean density and fuel mass.

10 Claims, 1 Drawing Sheet

PRIOR ART

METHOD AND APPARATUS FOR ULTRASONIC MEASUREMENT OF FUEL QUANTITY AND DENSITY

BACKGROUND OF THE INVENTION

This invention relates to fluid-quantity measurement systems and methods.

The invention is more particularly concerned with fluid-quantity measurement systems and methods employing ultrasonic probes with multiple reflectors.

In ultrasonic fluid quantity measurement systems, an ultrasonic transducer is mounted at the bottom of a vertical tube or still well, which is filled with fluid to the same height as fluid outside the tube. Examples of ultrasonic fluid-gauging systems are described in U.S. Pat. No. 2,990,543, U.S. Pat. No. 3,214,974, U.S. Pat. No. 3,290,944, U.S. Pat. No. 3,394,589, U.S. Pat. No. 3,693,445, U.S. Pat. No. 4,063,457, U.S. Pat. No. 4,183,007, U.S. Pat. No. 4,532,406, U.S. Pat. No. 4,748,846, U.S. Pat. No. 4,896,535, U.S. Pat. No. 4,909,080, U.S. Pat. No. 4,928,525, U.S. Pat. No. 5,095,747, U.S. Pat. No. 5,095,748, U.S. Pat. No. 5,119,676, U.S. Pat. No. 5,121,340, U.S. Pat. No. 5,127,266, U.S. Pat. No. 5,301,549, U.S. Pat. No. 5,309,763, U.S. Pat. No. 5,357,801, EP 138541, GB 2185575, GB 2247753, DE 3330059, JP 69024, WO 9119191, WO 9214996, SU 821939. The transducer transmits bursts of ultrasonic energy upwardly to the fluid/air interface where it is reflected back to the transducer. By measuring the time of travel of the bursts of energy, it is possible to calculate the height of the fluid surface. The speed of sound varies according to changes in fluid density and temperature. In order to compensate for this, it is usual practice for the still well to include a number of reflectors spaced apart along its length. Because the height of these reflectors is known, the ultrasonic reflections they produce can be used to calibrate the system and improve the calculation of the height and volume of fluid. In many applications, however, such as aircraft fuel gauging, it is necessary to know the mass of fuel, so a measurement of density is needed. Because of the temperature stratification that can occur within the fuel tank, there can be appreciable differences in the density of fuel at different heights, making it difficult accurately to calculate the fuel mass. The accurate measurement of fuel mass is of considerable importance to aircraft operators because it enables reduced quantities of fuel to be carried without reducing safety. This in turn enables greater payloads to be carried, with increased profitability.

BRIEF SUMMARY OF THE INVENTION

It is an object of the present invention to provide a fluid-quantity measurement system and method that can be used to alleviate this problem.

According to one aspect of the present invention there is provided a fluid-quantity measurement system including an ultrasonic probe having a plurality of reflectors spaced apart along its length, a densitometer arranged to provide a first measurement of fluid density, means for calculating a first speed of sound in the fluid, means for calculating a fluid constant from said first density and said first speed of sound, means for calculating the density of fluid at each reflector submerged in fluid from said fluid constant and from the speed of sound at that reflector, and means for calculating a mean density from the density calculations at each reflector submerged in the fluid.

The densitometer is preferably mounted towards the lower end of a tank in which the probe is mounted. The densitometer may be a vibrating cylinder densitometer. The means for calculating the fluid constant preferably calculates the constant from the expression $F=\rho \cdot v_1 \cdot B$, where F is the fluid constant, $\rho$ is the density, $v_1$ is the speed of sound, and B is a constant. The constant B is preferably approximately $0.1811$ $kg.sec.m^{-4}$. The system may calculate a weighted mean density by applying a weighting factor to each density measurement, the weighting factor being dependent on the volume of fluid at each reflector. The system may include a plurality of probes and may include means for providing an output representative of mass of fluid.

According to another aspect of the present invention there is provided a method of measuring fluid quantity comprising the steps of: measuring fluid density to provide a first measurement of fluid density, measuring the speed of sound in the fluid to provide a first speed of sound, calculating a fluid constant from the first measurement of fluid density and the speed of sound, transmitting bursts of ultrasonic energy upwardly through the fluid, receiving reflections of the bursts of energy from the fluid surface and from reflectors submerged in the fluid, calculating the height of the fluid surface from the signals transmitted from the fluid surface, calculating the speed of sound at each of the submerged reflectors from the time between transmission of the bursts of energy and reception of reflections from the reflectors, calculating the density of fluid at each reflector from the speed of sound at said reflector and the fluid constant, and calculating the mean density of fluid from the densities at each submerged reflector.

An aircraft fuel-gauging system and its method of operation, in accordance with the present invention, will now be described, by way of example, with reference to the accompanying drawing.

DETAILED DESCRIPTION OF THE PREFERRED EMBODIMENT

Figure 1:
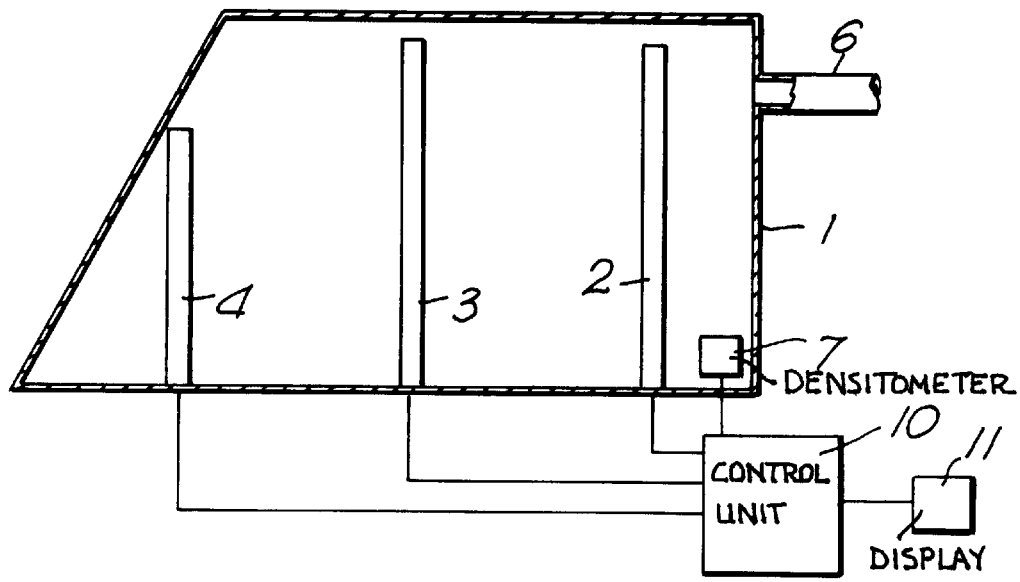
FIG. 1 illustrates schematically the system.

With reference first to FIG. 1, the fuel-gauging system includes a tank 1, which is typically located in a wing of the aircraft and is of irregular shape, containing several ultrasonic fuel gauging probes of which three probes 2 to 4 are shown. Tile tank 1 also has an inlet 6, by which fuel is supplied to the tank, and a densitometer 7. The probes 2 to 4 are connected to a control unit 10, which also receives the output from the densitometer 7, and provides an output indicative of fuel mass to a display 11 or other utilization means.

Figure 2:
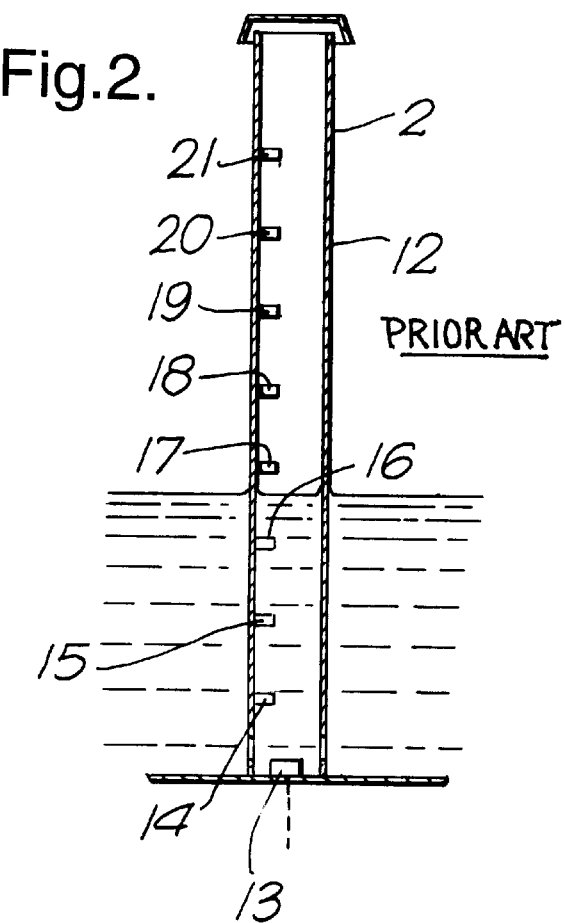
FIG. 2 is a cross-sectional side elevation of a probe in the system.

With reference now to FIG. 2, there is shown an example of a conventional ultrasonic probe 2, such as of the kind described in GB 2265219, GB 2265005 or GB 2270160. The probe 2 has an outer tube or still well 12, which is open at the top and bottom, so that fuel in the still well is at the same height as fuel outside the probe. An ultrasonic transducer 13 is located at the bottom of the still well 12 and transmits bursts of ultrasonic energy upwardly along the still well when energized by the control unit 10. The probe 2 has eight reflectors 14 to 21 mounted on the inside of the still well spaced apart along its length. The reflectors 14 to 21 take the form of short pegs or studs projecting across about one third of the diameter of the still well. Ultrasonic energy is reflected off the lower three reflectors 14 to 16 that are submerged in fuel and, because these reflected signals are produced from reflectors at known heights, they provide calibration signals for the probe in the manner described in GB 2265219.

The densitometer 7 may be of any conventional kind, such as a vibrating cylinder densitometer and, when the aircraft is refuelled, it provides an output to the control unit 10 representative of the density of fuel in the tank 1. However, it will be seen that it can only provide a density measurement $\rho$ at a single point, shown in FIG. 1 as being at the bottom of the tank 1, adjacent the probe 2. The control unit 10 receives the output of the densitometer 7 and also receives an output from the adjacent probe 2. The control unit 10 identifies the reflection from the lowest reflector 14, which is the one closest to the densitometer 7, and from this calculates the speed of sound $v_1$ over the region between the transducer 13 and the first reflector 14. The control unit 10 then calculates a value of a fuel or fluid constant F using the following expression:

$$F = \rho - v_1 \cdot B \tag{1}$$

where B is a constant equal to $3.84 \times 10^{-5}$ lb.sec.inch$^{-1}$ .USgallon$^{-1}$ or 0.1811 kg.sec.m$^{-4}$.

This fuel constant F is then used in subsequent calculations of fuel mass to calculate different measures of density at different fuel heights for all three probes 2 to 4. More particularly, rearranging expression (1) above gives:

$$\rho = F + v_1 \cdot B \tag{2}$$

so the density $\rho_n$ at the nth reflector would be given by:

$$\rho_n = F + v_n \cdot B \tag{3}$$

where $v_n$ is the speed of sound at the nth reflector.

In this way, an estimate of the density of fuel at each reflector can be calculated for use in calculations of the fuel mass. The control unit 10 calculates the weighted mean density for all the reflectors submerged in fuel, applying a weighting factor W, which is proportional to the volume of fuel at the reflector. In the present example, the tank tapers inwardly up one side so its cross-sectional area decreases with height and the volume of fuel around any one reflector, thereby, decreases with increasing height. The density weighting with the present tank, therefore, decreases with increasing height. In tanks of different shape, the weightings would be different. The weighted density $\rho_W$ for the illustrated probe 2, with three submerged reflectors 14 to 16 is given by the expression:

$$\rho_W = (W_1 \cdot \rho_1 + W_2 \cdot \rho_2 + W_3 \cdot \rho_3)/3 \tag{4}$$

where $W_3 > W_2 > W_1$ and where $W_1$ to $W_3$, and $\rho_1$ to $\rho_3$ are the weightings and densities of the reflectors 14 to 16 respectively.

The control unit 10 computes the position of the fuel surface from the height outputs of the three probes 2 to 4 and from this, and knowledge of the shape of the tank 1, calculates the volume of fuel in the tank. The control unit 10 then uses the weighted density $\rho_W$ and the volume to compute the fuel mass. The system may use the outputs from all three probes 2, 3 and 4 in order to compute the weighted fuel density, or only one probe 2.

Previous attempts to estimate density have used the speed of sound from only the uppermost submerged reflector to estimate an average density of the fuel but this does not give a sufficiently accurate estimation in many cases.

It will be appreciated that the present invention is not confined to fuel gauging applications but could be used in any ultrasonic fluid gauging system. In some applications it may not be necessary to compute fluid mass but it may still be desirable to have an indication of fluid density and its height or volume.

What I claim is:

1. A fluid-quantity measurement system comprising: a fluid tank; an ultrasonic probe mounted in said tank, said probe having a plurality of reflectors spaced apart along its length; a densitometer arranged to provide a first measurement of fluid density; and a control unit connected with said probe and said densitometer, said control unit being arranged to calculate: a first speed of sound in the fluid, a fluid constant from the measured first density and said first speed of sound, the density of fluid at each reflector submerged in fluid from said fluid type constant and from the speed of sound at that reflector, and a mean density from the density calculations at each reflector submerged in the fluid.

2. A system according to claim 1, wherein said densitometer is mounted towards the lower end of said tank.

3. A system according to claim 1, wherein said densitometer is a vibrating cylinder densitometer.

4. A system according to claim 1, wherein said control unit calculates the fluid type constant from the expression $F = \rho - v_1 \cdot B$, where 1 is the fluid type constant, $\rho$ is the density, $v_1$, is the speed of sound, and B is a constant.

5. A system according to claim 4, wherein the constant B is approximately $3.84 \times 10^5$ lb.sec.inch$^{-1}$ .USgallon$^{-1}$.

6. A system according to claim 1, wherein said control unit calculates a weighted mean density by applying a weighting factor to each density measurement, and wherein said weighting factor is dependent on the volume of fluid at each said reflector.

7. A system according to claim 1 including a plurality of probes.

8. A system according to claim 1, wherein said control unit provides an output representative of mass of fluid.

9. A fuel-gauging system comprising: a fuel tank; a plurality of ultrasonic probes mounted in said tank, each said probe having a plurality of reflectors spaced apart along its length; a densitometer arranged to provide a first measurement of fuel density; and a control unit connected with said probes and said densitometer, said control unit being arranged to calculate: a first speed of sound in the fuel, a fuel type constant from the measured first density and said first speed of sound, the density of fuel at each submerged reflector of at least one of said probes from said fuel constant and from the speed of sound at that reflector, a weighted mean density from the density calculations at each submerged reflector of at least one of said probes and a weighting factor dependent on the volume of fuel at each reflector, and a total mass of fuel in the tank from the outputs of each probe and the weighted mean density.

10. A method of measuring density of a fluid quantity comprising the steps of: measuring fluid to provide a first measurement of fluid density, measuring the speed of sound in said fluid to provide a first speed of sound, calculating a fluid constant from said first measurement of fluid density and said speed of sound, transmitting bursts of ultrasonic energy upwardly through said fluid, receiving reflections of said bursts of energy from the fluid surface and from reflectors submerged in the fluid, calculating the height of the fluid surface from the signals transmitted from the fluid surface, calculating the speed of sound at each of said submerged reflectors from the time between transmission of the bursts of energy and reception of reflections from said reflectors, calculating the density of fluid at each said reflector from the speed of sound at said reflector and said fluid constant, and calculating the mean density of fluid from said densities at each submerged reflector.

* * * * *